(12) United States Patent
Barten

(10) Patent No.: US 6,308,456 B1
(45) Date of Patent: Oct. 30, 2001

(54) METHOD FOR IMPROVING THE FORMING OF FLOWERS OF A GARLIC PLANT

(75) Inventor: Piet Barten, Noord-Scharwoude (NL)

(73) Assignee: Bejo Zaden B.V., ZH Warmenhuizen (NL)

( * ) Notice: Subject to any disclaimer, the term of this patent is extended or adjusted under 35 U.S.C. 154(b) by 0 days.

(21) Appl. No.: 09/403,504

(22) PCT Filed: Apr. 23, 1998

(86) PCT No.: PCT/NL98/00228

§ 371 Date: Feb. 28, 2000

§ 102(e) Date: Feb. 28, 2000

(87) PCT Pub. No.: WO98/47371

PCT Pub. Date: Oct. 29, 1998

(30) Foreign Application Priority Data

Apr. 23, 1997 (NL) .................................................. 1005881

(51) Int. Cl.⁷ ................................. A01H 3/04; A01G 7/00
(52) U.S. Cl. ............................................................ 47/58.1
(58) Field of Search ............................... 47/58.1; 800/321

(56) References Cited

U.S. PATENT DOCUMENTS

| 5,746,024 | * | 5/1998 | Rice et al. | 47/58.1 |
| 5,913,729 | * | 6/1999 | Kajimura | 47/58.1 |

OTHER PUBLICATIONS

Tizio, Ricardo. 1979. Floraison in vitro de l'Ail. C.R. Acad. Sc. Paris, t 289.*

* cited by examiner

Primary Examiner—Peter M. Poon
Assistant Examiner—Jeffrey L. Gellner
(74) Attorney, Agent, or Firm—Dorsey & Whitney LLP

(57) ABSTRACT

A garlic plant (*Allium sativum* L.) provided with an agent containing a hormone for improving the forming of flowers, at least substantially without bulbils, which has been added thereto in vivo prior to the forming of flowers, which hormone is selected from the group of gibberellins, preferably gibberellic acid type GA3. The agent containing the hormone is for example injected into the flower stalk of the garlic plant.

10 Claims, No Drawings

METHOD FOR IMPROVING THE FORMING OF FLOWERS OF A GARLIC PLANT

The invention relates to a method for improving the forming of flowers of a garlic plant (*Allium sativum* L.), that is, for effecting a normal development of flowers with garlic. This improved forming of flowers in accordance with the invention now makes it possible to improve garlic via sexual hybridization and multiply it on a commercial scale via seeds.

Commercially, garlic is an important crop, which, like onion, shallot and leek, belongs to the Allium family. In 1987 approx. 2,662,000 tons of garlic were produced worldwide, which corresponds to a crop area of approx. 421,000 hectares. Commercial garlic production takes place by means of vegetative propagation, whereby "garlic cloves", which are also fit for consumption, are used as propagation material. So far it has appeared to be impossible to effect practically acceptable generative propagation of garlic, since this crop forms hardly any flowers, and thus seeds, (if at all). The fact is that a garlic plant develops vegetative parts in the inflorescence, which parts have a strong impeding effect on the development of flowers. Said vegetative parts may be considered to be small "garlic cloves", and they are also referred to as "bulbils" or "topsets". Accordingly, attempts to produce commercial quantities of garlic seed have so far been unsuccessful.

There are significant drawbacks attached to vegetative propagation of garlic. The garlic cloves which function as propagation material are voluminous, which leads to high transport costs, whilst in addition they do not keep very well. Furthermore, vegetative propagation stands in the way of adequate crop improvement. Moreover, there is always a risk of virus diseases, nematodes and fungi being transferred from a parent plant.

A method for improving the forming of flowers of a garlic plant (*Allium sativum* L.) is known per se. With the known method, the aforesaid bulbils are manually removed from the inflorescence, so that in practice only a small part of the flowers have a chance of developing in a reasonable manner. After pollination of the flowers, seed formation takes place to a greater or lesser degree. One drawback of the known method is the fact that it is not only labour-intensive, but that in addition the inflorescences are damaged upon removal of the bulbils, which results in reduced seed formation. A few examples are mentioned in the relevant literature. Etoh et al. (1988) obtained 3000 seeds from various plants of a total of 16 different strains of garlic. On average approx. 10–20 seeds per plant were produced. M. R. Pooler and P. W. Simon (1994) only succeeded in obtaining 63 seeds from 1950 inflorescences of 11 different garlic strains.

The object of the invention is to provide a method for improving the forming of flowers of a garlic plant (*Allium sativum* L.), wherein no manual removal of bulbils takes place, but wherein flowers develop normally in the inflorescence all the same, so that the usual pollination by insects can take place, and a satisfactory seed formation can thus be effected.

In order to accomplish that objective, a method of the kind referred to in the introduction is according to the invention characterized in that an agent containing a hormone is added to the plant in vivo before the forming of flowers takes place. The agent is preferably a solution of the hormone in water. The hormone is in particular selected from the group of gibberellins. Preferably the hormone is gibberellic acid type GA3. Surprisingly, an extensive research has made it clear to the Applicant that the formation and the development of the aforesaid bulbils in the inflorescence of garlic results from a deviating hormone management in the plant. This has led to the insight that it must be possible to effect a change in the build-up and the composition of the inflorescence of the garlic plant by adjusting the hormonal balance by in vivo addition of the agent containing the hormone. Surprisingly, the aforesaid research has shown that adjusting the hormonal balance after the forming of flowers has taken place has hardly any effect, if at all, on the forming and the development of the bulbils. In this context the term forming of flowers is understood to mean inflorescence, that is, the forming of at least dozens of garlic flowers. The Applicant has been led by the following basic principles in the aforesaid research:

in order to produce sufficient garlic plant seeds for improvement and for commercial purposes, it is necessary in any case to obtain a normal inflorescence of the plant, a normal development of flowers in the inflorescence of garlic plants can only be obtained if the formation of bulbils in the inflorescence is prevented entirely or to a large degree.

The invention makes it possible to harvest commercial quantities of seed and thus to propagate garlic plants by a generative method. As already said before, generative propagation according to the invention makes it possible to give a plant various desired properties from another garlic plant by hybridization, whereby also the risk of virus diseases, nematodes and pathogenic fungi being transferred from a parent plant to the seed is prevented, or at least strongly reduced.

The Applicant has established by experiment that there are significant differences in the flower development of garlic strains that have been collected worldwide. Only those genotypes that were in principle capable, whether or not partially, of forming flowers were used as starting material.

The invention also relates to the agent containing the hormone for improving the forming of flowers with a garlic plant (*Allium sativum* L.). The agent is preferably a solution of the hormone in water. As already said before, the hormone has been selected in particular from the group of gibberellins, preferably gibberellic acid type GA3, gibberellin type GA4, or gibberellin type GA7. Satisfactory results were also obtained with a mixture of gibberellin types GA4 and GA7.

The invention also relates to a garlic plant (*Allium sativum* L.) as such, which is provided with the agent containing the hormone for improving the forming of flowers, at least substantially without bulbils, which has been added thereto in vivo prior to the forming of flowers.

Finally, the invention relates to parts of plants, among which plant cells, bulbils or garlic cloves, and to seeds of the garlic plant (*Allium sativum* L.) as defined above.

Within the framework of the research conducted by the Applicant, garlic was treated with various plant hormones in various concentrations en in various manners.

The following hormones were used:
1. IAA: Indolic Acetic Acid. 1 H indole-3-acetic acid. CAS 87-51-4.
2. IBA: Indolic Butyric Acid. 1 H indole-3-butanoic acid. CAS 133-32-4.
3. GA3: Gibberellic Acid A3/Gibberellin A3; 2,4a,7-trihydroxy-1-methyl-8-methylenegibb-3-ene-1,10-dicarboxylic acid 1.4a-lactone; CAS 77-06-5 or $C_{19}H_{22}O_6$.

For the sake of convenience, lest the description below becomes unnecessarily complicated, the description is based on the use of gibberellic acid type GA3. Good results were achieved with a hormone GA3 concentration ranging from 1 to 100 mg/l, in particular from 1 to 10 mg/l, preferably approx. 1 to 2 mg/l. It is explicitly noted that also other types of gibberellin may be used, such as GA4($C_{19}H_{24}O_5$; CAS 468-44-0) en GA7($C_{19}H_{22}O_5$; CAS 510-75-8), or combinations of two or more of such gibberellic acids, in particular selected from the group consisting of types GA3, GA4 and GA7. In that case the total concentrations will be within the above preferred ranges.

The hormones were added in vivo in the following manners:

a: Injection of a solution into the flower stalk, just below the flower bud:

Hormone solutions of 1% (w/v) in water were used. Some plants of the garlic strains were treated at three different points in time, whilst other plants of the same strain were only treated at one point in time. Each time three injections were given. At the time the various treatments took place, the plants were in a stage of development in which the flower buds were still confined in the so-called "beak-shaped" spathe.

b. Pouring a solution at the feet of plants which have grown in garden mould in pots:

An amount of 100 ml of a hormone solution was added to each pot by pouring. Each plant was treated once.

c. Cutting off the flower stalk from the plant and putting it in a hormone solution:

This experiment was carried out in two variants. The first time the cut-off flower stalks were put in 300 ml of a hormone solution for four days. Then they were transferred to water. The second time the flower stalks were transferred to water after one day already.

Surprisingly, an extensive research conducted by the Applicant has furthermore shown that the manner in which the hormones are added to the plants has practically no influence on the result. Apparently the transport of the added hormones to the inflorescence takes place from all parts of the plant. These tests have confirmed that inflorescences indeed develop normally when the formation and the development of the bulbils in the inflorescence is prevented.

The invention will be explained in more detail hereafter by means of the preferred examples discussed below:

EXAMPLE 1

Obtaining Starting Material

Various garlic strains are maintained in a vegetative manner. The planting out of garlic cloves (vegetative parts) takes place in the month of October. The vegetative growth of the plants takes place until the winter months. During the winter, when temperatures are low, growth is stopped more or less, and the plant is vernalised. During this process, flower induction takes place in the plant. Growth continues in the spring that follows, and the generative parts of the plant develop. The development of the flower stalks starts in the period of May/June, and flowering starts in July.

EXAMPLE 2

The Garlic Strains Used for Testing

The following garlic strains were used for testing according to method a (injection into the flower stalk): W6171, W6172, W6173, W6174, W6175, W6176, W6177, W6178, W6179, W6180, W6181, W6182, W6183, W6184, W6185, W6186, W6187, W6188, W6189, W6190, W6191, W6192.

The following garlic strains were used for testing according to method b (pouring at the foot of the plant): W6178, W6180, W6186.

The following garlic strains were used for testing according to method c (cut-off flower stalk in beaker): W6171, W6172, W6173, W6174, W6176, W6178, W6180, W6181, W6182, W6184, W6185, W6191.

EXAMPLE 3

Preparation of the Hormone Solutions

Relatively high hormone concentrations were used in this research, whereby it was expected that this would more clearly show the influence of the hormones that were used on the flower development. In a next research it can be determined exactly at what minimum concentration a satisfactory effect can still be obtained. The starting point thereby is that it must be strived at to keep the eventual concentration of the hormones to be used as low as possible, in order to minimise the occurrence of any unexpected, adverse side effects of the hormones.

In this research solutions of 0.5 and 1.0% (weight/volume) of plant hormones IAA, IBA and GA3 were used, which corresponds with 0.5 and 1.0 g respectively per 100 ml of water.

EXAMPLE 4

The Addition of the Hormone Solutions

Method a:

With this method, a solution of (1% w/v) of the hormones was used. Some plants of the garlic strains were treated on three different dates, other plants were only treated on one of said dates. Each time three injections were given, whereby about three drops (0.06 ml) of the hormone solution were introduced into the stalk per injection. It has become apparent that the effect obtained with one treatment is the same as the effect obtained with three treatments. Apparently the concentration of 1% (w/v) is so high that the effect is achieved after one treatment already. The dates of the treatments were: Jun. 20, 1996, Jun. 24, 1996 and Jul. 3, 1996. The hormones used were IAA, IBA and GA3.

Method b:

The addition of 100 ml of a 0.5% (w/v) solution was carried out with all three types of hormones. The solutions was poured at the foot of the plant, and absorbed by the soil surrounding the roots, on Jun. 20, 1996. In this way it was attempted to give the roots the chance to take up the hormones and transport them to other parts of the plant, including the inflorescence. The hormones used were IAA, IBA and GA3.

Method c:

With this method, the cut-off flower stalks were put in 300 ml of a 0.5% (w/v) hormone solution. On Jun. 20, 1996 this took place for the first time for a period of four days, and on Jul. 3, 1996 other flower stalks were treated for a period of one day. After the respective treatments the flower stalks were transferred to plain water. Also in this case it has become apparent that the concentration that was used was high enough to achieve the effect after one day already. As it is, the effect achieved after four days is identical to the effect achieved after one day. The hormones used were IAA, IBA and GA3.

Method d:

With this method, plants having developed roots were immersed in hormone solutions of 0.1, 0.5 and 1% (w/v) of the hormones used after the low-temperature period as described in example 1. At this stage the plants have 5–6 leaves, and the induction of the inflorescence has already taken place.

Method e:

With this method, garlic cloves, still being in a vegetative state, are immersed in hormone solutions of 0.1, 0.5 and 1% (w/v) of the hormones used prior to the low-temperature period. Said immersion takes place for a period of maximally 24 hours. Following said immersion, the cloves are planted in October and further treated as described in example 1.

The treatments described under d and e were carried out on the following strains:

| | | |
|---|---|---|
| Kau94017A | Fru94015A | Fru94009A |
| Fru94156C | Fru94133A | Fru94089A |
| Fru94077A | Sov93004A | Kau93012A |
| Fru93046a | | |

EXAMPLE 5

Description of the Observations

The evaluation of the influences of the various hormones and the methods of adding them to the garlic plants took place in the period between Jul. 26, 1996 and Aug. 9, 1996. The point in time was selected in dependence on the state of development of the inflorescence.

When the test results are studied, it becomes apparent that there is a connection between the forming of bulbils in the inflorescence and the forming of flowers in the inflorescence. When the number of bulbils in the inflorescence decreases, the inflorescence develops more normally (read: more flowers per inflorescence), because the flowers are not pushed aside, which allows them to develop fully.

For the analysis of the test results the following evaluation scale was used, which varied from 0 to 4.

The 5 classes are described as follows:

0 Very strong development of bulbils in the inflorescence. No normally developed flowers in the inflorescence.

1 Less strong development of bulbils in the inflorescence. A few (fewer than 10) normally developed flowers in the inflorescence.

2 Moderate development of bulbils in the inflorescence. An increase (between 10 and 50) of the number of normally developed flowers in the inflorescence.

3 A strong reduction of the development of bulbils in the inflorescence. A strong increase (between 50 and 100) of the number of normally developed flowers in the inflorescence.

4 Hardly any development of bulbils, if at all, in the inflorescence. A large to very large (more than 100) number of normally developed flowers in the inflorescence.

EXAMPLE 6

Results of the Evaluation According to the Scale Described in Example 5

Results according to method a:

| | METHOD A | | | | |
|---|---|---|---|---|---|
| clone no. | untr. | man. | IAA | IBA | GA3 |
| W 6171 | 0 | 1 | 1 | 1 | 3 |
| W 6172 | 1 | 3 | 1 | 0 | 4 |
| W 6173 | 0 | 1 | 1 | 0 | 4 |
| W 6174 | 1 | 2 | 1 | 0 | 2 |
| W 6175 | 1 | 2 | 2 | 0 | 4 |
| W 6176 | 1 | 2 | 0 | 0 | 4 |
| W 6177 | 0 | 1 | 1 | 0 | 4 |
| W 6178 | 1 | 3 | 1 | 0 | 4 |
| W 6179 | 0 | 1 | 1 | 0 | 3 |

-continued

| | METHOD A | | | | |
|---|---|---|---|---|---|
| clone no. | untr. | man. | IAA | IBA | GA3 |
| W 6180 | 0 | 2 | 1 | 0 | 2 |
| W 6181 | 0 | 1 | 0 | 0 | 4 |
| W 6182 | 0 | 1 | 0 | 0 | 2 |
| W 6183 | 0 | 1 | 1 | 0 | 2 |
| W 6184 | 0 | 2 | 1 | 0 | 3 |
| W 6185 | 0 | 2 | 1 | 0 | 3 |
| W 6186 | 0 | 2 | 1 | 0 | 3 |
| W 6187 | 0 | 2 | 0 | 0 | 4 |
| W 6188 | 0 | 2 | 1 | 0 | 2 |
| W 6189 | 0 | 1 | 1 | 0 | 2 |
| W 6190 | 0 | 2 | 1 | 0 | 4 |
| W 6191 | 0 | 2 | 1 | 0 | 3 |
| W 6192 | 0 | 2 | 1 | 0 | 3 | untr. = untreated
man. = manual

Results according to method b:

| | METHOD B | | | | |
|---|---|---|---|---|---|
| clone no. | untr. | man. | IAA | IBA | GA3 |
| W 6178 | 1 | 3 | 1 | 1 | 3 |
| W 6180 | 0 | 2 | 1 | 1 | 3 |
| W 6186 | 0 | 2 | 1 | 1 | 3 | untr.. = untreated
man. = manual

Results according to method c:

| | METHOD C | | | | |
|---|---|---|---|---|---|
| clone no. | untr. | man. | IAA | IBA | GA3 |
| W 6171 | 0 | 1 | — | — | 3 |
| W 6172 | 1 | 3 | — | — | 3 |
| W 6173 | 0 | 1 | — | — | 3 |
| W 6174 | 1 | 2 | — | — | 2 |
| W 6176 | 1 | 2 | — | 1 | — |
| W 6178 | 1 | 3 | — | — | 3 |
| W 6180 | 0 | 2 | 1 | — | — |
| W 6181 | 0 | 1 | 1 | — | — |
| W 6182 | 0 | 1 | — | 0 | — |
| W 6184 | 0 | 2 | — | 0 | — |
| W 6185 | 0 | 2 | — | 0 | — |
| W 6191 | 0 | 2 | — | 0 | — | untr. = untreated
man. = manual

EXAMPLE 7

The Influence of Hormones IBA, IAA and GA3 on the Inflorescence of Garlic After the Addition According to Methods a, b and c and the Occurrence of Any Side Effects Method a:

Treatment with IBA does not result in any reduction of the number of bulbils in the inflorescences. Practically all scores are equal to those of the untreated ones. A striking side effect of IBA was observed, however: The bulbils in the inflorescence became larger, obviously because stretching of cells took place as a result of the addition of said hormone. Treatment with IBA is not an alternative for the manual removal of the bulbils.

Treatment with IAA shows a very slight improvement. The development of the bulbils takes place slightly more slowly than that of untreated check specimens. In comparison with manual removal of the bulbils, the effect of treatment with IAA is inadequate, however. Also in this case, there is apparently a side effect in the form of cell stretching in the bulbils, albeit to a lesser extent than is the case of treatment with IBA.

Treatment with gibberellic acid GA3 shows a distinct reduction of the extent to which bulbils are formed in the inflorescence of garlic. In all cases the development of the inflorescence is superior to that of the untreated check specimens, the specimens treated with IAA and the specimens treated with IBA. Furthermore, with 20 of the total number of 22 treated garlic strains a distinct improvement in the development of the inflorescence can be observed. Only in two cases the development is equal to the case where the bulbils were removed manually.

From the average score it appears that treatment with GA3 is the only treatment that has a distinct and almost maximal effect on a desired development of the inflorescence.

Untreated: average score 0.2
Manual: average score 1.7
IAA: average score 0.8
IBA: average score 0.0
GA3: average score 3.1
Method b:

Also in this case the addition of hormones according to method b shows clearly that the influence of IAA and IBA is practically neglectable. Treatment with GA3 has a distinctly positive effect. The number of bulbils in the inflorescence strongly decreases, whereas the number of flowers that normally develop strongly increases.

A side effect that was observed after treatment with IAA and IBA was accelerated ageing of the leaf in comparison with the untreated check specimens. This effect was not observed after treatment with GA3.

When the average scores obtained with method b are studied, it can be concluded that GA3 has a positive effect on the development of the inflorescence.

Untreated: average score 0.3
Manual: average score 2.3
IAA: average score 1.0
IBA: average score 1.0
GA3 average score 3.0
Method c:

With this method, the irregular increase of the extent of cell stretching became apparent after the addition of IAA and IBA. The flower stalk stretches and exhibits all kinds of irregular twisting. Also the bulbils in the inflorescence are clearly stretched, and their number is practically identical to that of the untreated check specimens. These effects do not occur when the plants are treated with GA3. With the passage of time, the differences between manual removal of the bulbils and treatment with GA3 became more distinct, with GA3 showing the better result. With this treatment, the development of the bulbils in the inflorescence was strongly contained, and the flowers in the inflorescence were able to develop properly.

When the average scores are studied, it becomes apparent that treatment with GA3 is the only treatment that produces a satisfactory result.

Untreated: average score 0.3
Manually: average score 1.8
IAA: average score 1.0
IBA: average score 0.2
GA3: average score 2.8

EXAMPLE 8

Average Seed Count

The table below shows the average seed count per flower bud per garlic plant in the case of mass multiplication. The number of garlic plant strains is plotted horizontally, whilst the various treatments are plotted vertically. It is apparent that the best results were obtained with strains Fru94077c en Fru94156.

| | Strain Fru93046A | Kau93012A | Sov93004A | Fru 94077C |
|---|---|---|---|---|
| 1 mg/l GA3 | — | 2 | — | 73 |
| 10 mg/l GA3 | — | 1 | — | 65 |
| 100 mg/l GA3 | — | 16 | 3 | 62 |
| 1000 mg/l GA3 | — | — | — | 1 |

| | Strain Fru94089A | Fru94133A | Fru94156C | Fru 94009A |
|---|---|---|---|---|
| 1 mg/l GA3 | 42 | 77 | 37 | 11 |
| 10 mg/l GA3 | 38 | 56 | 86 | 3 |
| 100 mg/l GA3 | 11 | 45 | 72 | 5 |

| | Strain Fru94015C | Kau94017A |
|---|---|---|
| 1 mg/l GA3 | 45 | |
| 10 mg/l GA3 | 16 | |
| 100 mg/l GA3 | 12 | |

What is claimed is:

1. An agent containing a hormone for improving the forming of flowers of a garlic plant (*Allium sativum* L.) and to increase grain yield.

2. An agent according to claim 1, wherein said hormone is selected from the group of gibberellins.

3. A method according to claim 2, wherein said hormone is gibberellic acid type GA3, gibberellin type GA4, or gibberellin type GA7.

4. A method for improving the forming of flowers of a garlic plant (*Allium sativum* L.), to improve grain yield characterized by adding an agent containing a hormone to the plant in vivo before the forming of flowers takes place.

5. A method according to claim 4, wherein said hormone is selected from the group of gibberellins.

6. A method according to claim 5, wherein said hormone is gibberellic acid type GA3, gibberellin type GA4, or gibberellin type GA7.

7. A garlic plant (*Allium sativum* L.), provided with an agent containing a hormone for improving the forming of flowers and to increase grain yield, at least substantially without bulbils, which has been added thereto in vivo prior to the forming of flowers.

8. A garlic plant (*Allium sativum* L.) according to claim 7, wherein said hormone is selected from the group of gibberellins.

9. A garlic plant (*Allium sativum* L.) according to claim 8, wherein said hormone is gibberellic acid type GA3, gibberellin type GA4, or gibberellin type GA7.

10. Plant parts, including plant cells, bulbils or garlic cloves, and seeds of a garlic plant (*Allium sativum* L.) according to any one of the preceding claims 7, 8 or 9.

* * * * *